(12) United States Patent
Gasparetto et al.

(10) Patent No.: US 12,005,126 B2
(45) Date of Patent: Jun. 11, 2024

(54) COMPOSITIONS FOR ORAL ADMINISTRATION OF PENTOSAN POLYSULFATE IN FORM OF NANOPARTICLES WITH IMPROVED INTESTINAL ABSORPTION

(71) Applicant: NEXTRARESEARCH S.R.L., Rome (IT)

(72) Inventors: Adolfo Gasparetto, Rome (IT); Fabio Borella, Rome (IT); Viviana Mascilongo, Rome (IT); Ruggero Bettini, Parma (IT); Fabio Sonvico, Parma (IT); Marta Cito, Martina Franca (IT)

(73) Assignee: ALMIRA PHARMA SRL, Rome (IT)

( * ) Notice: Subject to any disclaimer, the term of this patent is extended or adjusted under 35 U.S.C. 154(b) by 604 days.

(21) Appl. No.: 17/255,603

(22) PCT Filed: May 16, 2019

(86) PCT No.: PCT/EP2019/062662
§ 371 (c)(1),
(2) Date: Dec. 23, 2020

(87) PCT Pub. No.: WO2020/001852
PCT Pub. Date: Jan. 2, 2020

(65) Prior Publication Data
US 2021/0260214 A1    Aug. 26, 2021

(30) Foreign Application Priority Data

Jun. 27, 2018  (EP) .................................... 18180223

(51) Int. Cl.
*A61K 31/737* (2006.01)
*A61K 9/00* (2006.01)
*A61K 47/61* (2017.01)
*A61K 47/69* (2017.01)

(52) U.S. Cl.
CPC ........ *A61K 47/6939* (2017.08); *A61K 9/0053* (2013.01); *A61K 31/737* (2013.01); *A61K 47/61* (2017.08); *A61K 47/6943* (2017.08)

(58) Field of Classification Search
None
See application file for complete search history.

(56) References Cited

U.S. PATENT DOCUMENTS

2007/0243218 A1   10/2007   Ellinghuysen et al.
2018/0037895 A1   2/2018    Merzouki et al.

FOREIGN PATENT DOCUMENTS

CN    1454588 A    11/2003

OTHER PUBLICATIONS

Raspagni A. et al., "A preliminary study of chitosan-pentosan polysulfate sodium complex as vaginal sustained drug delivery system in a rare disease treat", Journal of Controlled Release, vol. 148, No. 1, 2010, e118-e119.
Search Report and Written Opinion of PCT/EP2019/062662 dated Jul. 26, 2019.
Office Action cited in counterpart Chinese Patent Application No. 201980042637.8 dated Oct. 12, 2023.

*Primary Examiner* — Alton N Pryor
(74) *Attorney, Agent, or Firm* — Silvia Salvadori, P.C.; Silvia Salvadori

(57) ABSTRACT

The present invention relates to pharmaceutical composition for the oral delivery of Pentosan Polysulfate sodium (PPS). In particular, the invention discloses compositions of PPS in form of nanoparticles with a suitable polymer aimed to improve the PPS absorption in the small intestine and reduce or eliminate the side effects in the colon.

3 Claims, 1 Drawing Sheet

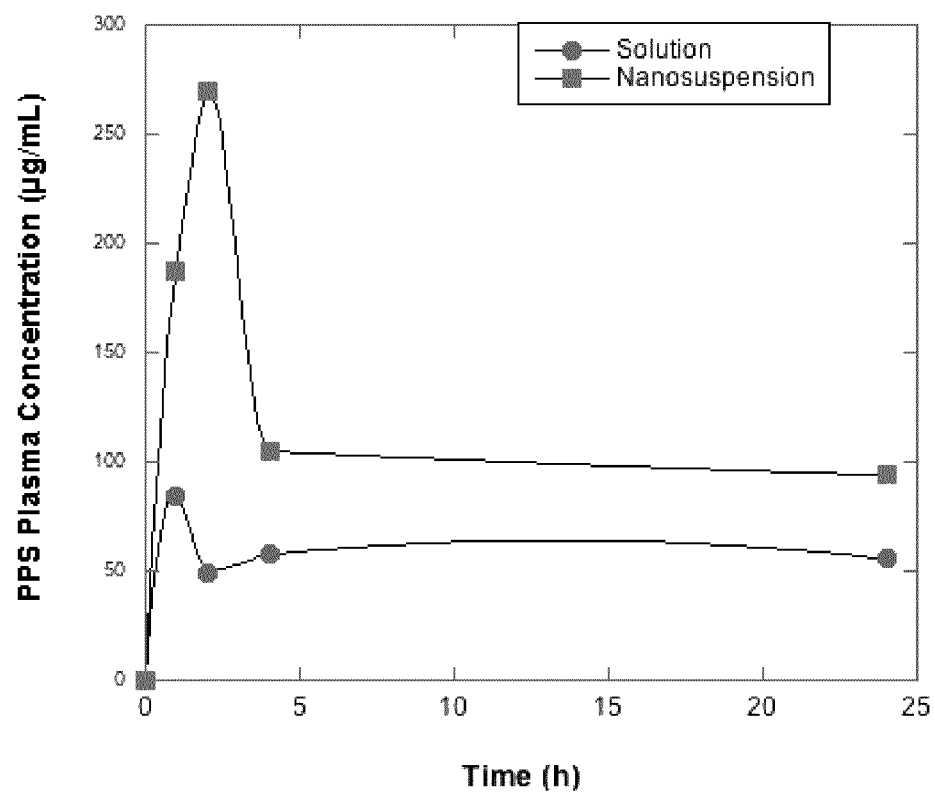

COMPOSITIONS FOR ORAL ADMINISTRATION OF PENTOSAN POLYSULFATE IN FORM OF NANOPARTICLES WITH IMPROVED INTESTINAL ABSORPTION

This application is a U.S. national stage of PCT/EP2019/062662 filed on 16 May 2019, which claims priority to and the benefit of European Application No. 18180223.2 filed on 27 Jun. 2018, the contents of which are incorporated herein by reference in their entireties.

FIELD OF THE INVENTION

The present invention relates to pharmaceutical composition for the oral delivery of Pentosan Polysulfate sodium (PPS). In particular, the invention discloses compositions of PPS in form of nanoparticles with a suitable polymer aimed to improve the PPS absorption in the small intestine and reduce or eliminate the side effects in the colon.

STATE OF THE ART

Pentosan Polysulfate sodium is a semi-synthetic, sulfated polysaccharide, chemically and structurally similar to heparin and glycosaminoglycans (GAGs). It is used as anti-inflammatory in patients with interstitial cystitis (IC) repairing damaged glycosaminoglycan (GAG) layers lining the urothelium to reduce the permeability in damaged parts of the barrier and preventing toxins from the urine irritating the uroepithelium. It can also reduce the inflammatory response and the histamine secretion through inhibition of connective tissue and mucosal mast cells.

When administered orally, it involves several side effects which are strongly limiting its acceptance by the patients. These side effects are mainly ascribable to the poor absorption of the drug in the upper part of the gastro intestinal tract; this results in a significant drug exposure to the colonic mucosa with consequent adverse effects mainly represented by diarrhea and bleeding.

EP2101799 discloses the use among other of PPS to prevent or treat inflammation associated to damage of connective tissue. No specific formulation approach is claimed or described in this document.

AU2012284048B2 discloses a method for enhancing blood coagulation with the use of non-anticoagulant sulfated polysaccharides (NASP) such as PPS. The goal is achieved by increasing the drug absorption upon oral administration of the formulation containing NASP and a permeation enhancer of the gastrointestinal epithelial barrier. Chitosan is described as an enhancer in a concentration ranging from 0.3 to 3%.

US2017189443 discloses a pharmaceutical composition for the administration of PPS containing a permeation enhancer to improve the intestinal absorption upon oral administration. Chitosan is not cited among said enhancers.

WO2016191698 discloses tablets containing PPS for the treatment of sickle cell disease. No specific formulation approach is mentioned in this document.

WO2016199161 discloses tablets formulation (without specific features) containing both PPS and an alpha adrenergic blocker for the treatment of bladder outlet obstruction.

Nanoparticles drug delivery system are nano-carriers used to deliver drugs. Compared with other forms of drug carriers, nanoparticles have many advantages in terms of bioavailability, reduced enzymatic degradation, toxicity or side effects. The interaction between oppositely charged polysaccharides is commonly exploited to form water insoluble complex (A. Nakayama and K. Shinoda J. Colloidal and Interface Sciences, 55, 1976, 126-132).

As an example, Grabovac and Bernkop-Schnurch proposed to improve the intestinal membrane permeability of low molecular weight heparin by complexation with stem bromelain (V. Grabovac and A. Bernkop-Schnurch Int. J. Pharm 326, 2006, 153-159).

Among polymers capable to give rise to nanoparticles, chitosan appears as the most promising cationic polymer potentially able to interact with the anionic active ingredient. For instance, chitosan has been proposed to form nanoparticles with heparin by polyelectrolyte complexation (Z. Liu et al. J. Biomed Mat. Res Part A; S. Boddoi et al. Biomacromolecules 10, 2009, 1402-1409).

Chitosan (CS) is a polycationic, non-toxic, mucoadhesive polymer, which has been proven to be safe. It can adhere to mucosa surface opening the tight junctions between epithelial cells, and therefore potentially capable to improve the drug absorption. It allows a prolonged interaction between the delivery system and the membrane epithelia, facilitating more efficient drug diffusion into the mucus/epithelium layer.

H. Abdel-Haq and E. Bossu have demonstrated the capability of chitosan to form complexes with PPS (J. Chromatography A 1257, 2012, 125-130), without disclosing the specific conditions for the formation of said complexes. No therapeutic application of the disclosed complexes has been described.

Raspagni et al. (J. Controlled Release 148, 2010, e112-e124) have described a preliminary study on the formation of complexes between PPS and chitosan by ionotropic gelation and in-vitro release of the drug. They proposed a composition in form of gel for topical (vaginal) application based on the weight ratio between PPS and chitosan: 0.5:1, 1.2:1, 2.2:1.

BRIEF DESCRIPTION OF THE DRAWINGS

FIG. 1 shows the plasma concentration v. time curves evaluated in an in-vivo pharmacokinetics study carried out in rats.

DETAILED DESCRIPTION OF THE INVENTION

The present invention concerns oral compositions comprising nanoparticles of a complex of Pentosan Polysulfate sodium (PPS) with chitosan. The compositions of the invention are preferably in form of tablets, hard capsules, granules or powders in a sachet, powders for extemporary preparation of a solution or syrups. The nanoparticles are obtained by self-assembling in solution due to ionic interaction between PPS and the ionizable functional groups of chitosan. Such interaction in aqueous solution results in the spontaneous formation of particles whose dimension depends upon the polymer characteristics and parameters, such as molecular weight, degree of substitution, concentration in the starting solution as well as on the parameters of the production process. The nanoparticles of the invention, having preferably a diameter between 80 and 220 nm measured by dynamic light scattering technique, directly permeate the epithelium of the upper part of the intestine in form of a stable intermolecular complex that can carry the active ingredient through the epithelial cell membrane by endocytosis of the whole nanoparticle rather than by diffusion of the free drug (A. Dube et al. Chitosan nanoparticles enhance the intestinal absorption of the green tea catechins (+)-catechin and (−)-epigallocatechin gallate, Eur. J. Phar, Sci. 41, 2019-225, 2010)). In this way, the amount of unabsorbed drug reaching the large intestine is significantly reduced and the colonic irritation lowered. This feature allows a significant reduction of the administered dose as a consequence of the improved absorption.

The formulations of the invention are typically prepared starting from a solution of PPS in water at concentration comprised from 1 to 10 mg/mL. An acidic aqueous solution of chitosan at pH ranging from 3 to 5.5 is added drop-wise into said PPS solution. The acid used for the preparation of said chitosan solution may be selected from hydrochloric acid, sulfuric acid, glutamic acid, lactic acid, ascorbic acid or any other physiologically acceptable acid capable to bring the polymer in solution at a concentration ranging from 1 and 6.5 mg/mL.

The ratio of the solutions of PPS to chitosan ranges from 3:6 v/v and 5:1.5 and is more preferably 4:5 v/v when both the solutions are concentrated 1 mg/mL. At higher concentrations of both the polyanions different ratio are preferred such as 5:1.5, 5:2, 5:3, 5:4 v/v.

The PPS solution is kept under stirring during the addition of the chitosan solution. Said stirring can be obtained with a paddle, a propeller, a magnetic stirrer, a turbo disperser or any other type of mixing equipment suitable for obtaining a high dispersion degree. When a paddle, a propeller or a magnetic stirrer is used, the rotation is kept between 300 and 1500 rotation per minute, preferably between 400 and 1200 and more preferably 500 and 1000 rpm, whereas in the case of the turbo disperser the preferred speed of the rotor ranges from 8000 and 30000 rpm.

The dispersion process is carried out at a temperature ranging from 20 to 60° C., preferably between 25 and 50° C. and more preferably at 40° C.

A further preparation step is required to reduce the nanoparticle dimension to the size of interest especially when the initial concentration of the two components is higher than 1 mg/mL. This step implies the use of processes such as high-pressure homogenization, nanomilling or any other process capable to reduce mechanically the dimension of the nanoparticles.

This step is of particular importance for the possible industrial exploitation of the present invention because it allows preparing nanosuspensions at high PPS concentrations, thus reducing significantly the time and the amount of energy needed for the subsequent transformation of the nanosuspension into a free-flowing powder.

When high-pressure homogenization is used, particles in the desired range can be obtained at pressure from 500 bar to 1500 bar and more preferably at 1200 bar. The temperature of the process can range from 40 to 60° C., preferably between 40 and 50° C. and more preferably is 40° C. The number of homogenization cycles can range from 5 to 50, more preferably from 10 to 40 and more preferable is 35.

Nanoparticles of the complex of PPS with chitosan having a size comprised 80-220 nm are obtained from a chitosan having a degree of deacetylation between 78 and 99%, preferably between 85 and 97% and more preferably between 92 and 96% and molecular weight (number average molecular mass) comprised between 30 and 400 kDa, preferably between 65 and 300 kDa and more preferably between 67 and 200 kDa.

The nanoparticles of the invention are characterized by a particularly high degree of complexation of PPS with chitosan. The non-complexed PPS in the nanosuspension obtained according to the invention upon interaction between the PPS solution and chitosan solution is lower than 20% by weight with respect to the nominal dose of PPS in the nanosuspension. The aspect mentioned above is twofold important as, from one side, it would guarantee that the PPS in the formulation is all in nanoparticle form, so that it can be entirely transported through the epithelium of the small intestine, and from the other side, that in case part of the nanoparticles would escape the mal intestine absorption, there would not be free PPS reaching the colon. In fact, since the nanoparticles form in an acidic solution, if one considers the solubility characteristics of chitosan, it comes out that the particle solubility product will be even lower at the slightly basic environment of the colon.

The obtained homogenized nanosuspension is then transformed into a free-flowing powder either by freeze drying, spray drying or dispersion/absorption on a solid carrier. In all cases, the nanosuspension is mixed with a pharmaceutically acceptable bulking agent capable to facilitate the re-dispersion of the nanoparticles in an aqueous fluid, such as the gastrointestinal one.

The bulking agent can be a sugar such as dextrose, glucose, fructose, lactose, sucrose, raffinose, trehalose, a polyol such as mannitol, sorbitol, a polymer such as cellulose, an oligomer such as dextrin, an inorganic salt such as calcium phosphate, magnesium carbonate, bentonite, kaolin.

The ratio between the volume of the suspension and the amount of bulking agent may vary within wide intervals and will be easily determined by the skilled person according to the common general knowledge.

The resulting free flowing powder is then transformed into a solid dosage form by a standard process to obtain tablets, hard capsules, granules or powders, powders for extemporary preparation of a solution, solutions or syrups. The nanoparticles of the invention are administered at a dose providing a therapeutic amount of PPS, typically in the range from 50 to 200 mg of PPS.

The absorption of the nanoparticles of the invention may be evaluated by in vitro permeation tests on monolayers of Caco-2 cells, according to the method disclosed by I. Hubatsch, E. Ragnarrson, P. Artursson in "Determination of drug permeability and prediction of drug absorption in Caco-2 monolayers", Nature Protocols vol. 2 n. 9, 2007, 2111-2119 and by Meunier V et al., in "The human intestinal epithelial cell line Caco-2; pharmacological and pharmacokinetic applications" Cell Biol Toxicol. 1995 August; 11(3-4):187-94.

The bioavailability of PPS from the formulations of this invention can be evaluated in rats upon oral administration by gavage of the powder dispersion in comparison to the solution of non-formulated PPS The effects on particle size of different chitosan molecular weights, degree of deacetylation, concentrations and process parameters are reported in the following examples.

Example 1

A volume of 8 mL of solution of PPS at the concentration of 1 mg/mL was added drop-wise to 10 mL of solutions of chitosan 95/50 (degree of deacetylation 97%, molecular weight 150 kDa, HMC, Germany) having different concentrations (0.5-5 mg/mL range), under constant stirring of 16800 rpm using a T10 basic Ultra-Turrax disperser (IKA, Germany). The mixing step was carried out at 40° C. for 2 minutes.

The particle size (mean zeta average), and size distribution (polydispersity index, PDI) of the formed particles were measured by dynamic light scattering technique (Zetasizer, Malvern Instrument, UK).

The obtained data are reported in Table 1.

TABLE 1

Particle size and size distribution of particles obtained 16800 rpm using a T10 basic Ultra-Turrax disperser as a function of concentration of the chitosan solution.

| Chitosan concentration (mg/mL) | Mean z-average (nm) | Polydispersity index |
|---|---|---|
| 0.5 | 182.5 | 0.222 |
| 1 | 184.3 | 0.237 |
| 1.5 | 319.5 | 0.431 |
| 2 | 479.9 | 0.661 |
| 2.5 | Solid precipitate | — |
| 5 | Solid precipitate | — |

The particle size as well as the size distribution increases with the concentration of the chitosan solution. It can be observed that with the adopted stirring conditions, particles in the size interval of interest (<220 nm) can be obtained with chitosan concentration ≤1 mg/mL.

Example 2

A volume of 8 mL of solution of PPS at the concentration of 1 mg/mL was added drop-wise to 10 mL of solutions of chitosan 75/50 (degree of deacetylation 76%, molecular weight 1280 kDa, HMC, Germany) having a concentration of 1 mg/mL, under constant stirring of 16800 rpm using a T10 basic Ultra-Turrax disperser (IKA, Germany). The mixing step was carried out at 40° C. for 2 minutes.

A solid precipitate consisting of particles in the µm range was obtained upon mixing.

Example 3

A volume of 16 mL of solution of PPS at the concentration of 1 mg/mL was added drop-wise to 20 mL of solutions of chitosan 95/50 (degree of deacetylation 97%, molecular weight 150 kDa, HMC, Germany) having a concentrations of 1 mg/mL, under variable magnetic stirring ranging from 200 and 950 rpm using a C-Mag magnetic stirrer (IKA, Germany). The mixing step was carried out at 40° C. for 3 minutes.

The particle size (mean zeta average), and size distribution (polydispersity index, PDI) of the formed particles were measured by dynamic light scattering technique (Zetasizer, Malvern Instrument, UK).

The obtained data are reported in Table 2.

TABLE 2

Particle size and size distribution of particles obtained at variable stirring rate using a magnetic stirrer staring from a chitosan solution of 1 mg/mL.

| Stirring rate (rpm) | Mean Z-average (nm) | Polydispersity index |
|---|---|---|
| 200 | 235.7 | 0.267 |
| 500 | 189.2 | 0.245 |
| 950 | 150.6 | 0.225 |

The particle size decreases with the increase of the stirring rate, so does the polydispersity index.

Particles in the size interval of interest (<220 nm) can be obtained starting from a PPS solution 1 mg/mL with magnetic stirring higher than 300 rpm.

Example 4

A volume of 12 mL of solution of PPS at the concentration of 1 mg/mL was added drop-wise to 15 mL of solutions of chitosan 95/50 (degree of deacetylation 97%, molecular weight 150 kDa, HMC, Germany) having a concentrations of 1 mg/mL, under variable rotor rotation, ranging from 800 to 25600 rpm using a T10 basic Ultra-Turrax disperser (IKA, Germany). The mixing step was carried out at 40° C. for 2 minutes.

The particle size (mean zeta average), and size distribution (polydispersity index, PDI) of the formed particles were measured by dynamic light scattering technique (Zetasizer, Malvern Instrument, UK).

The obtained data are reported in Table 3.

TABLE 3

Particle size and size distribution of particles obtained from 8000 and 25-600 rpm using a T10 basic Ultra-Turrax disperser starting from a chitosan solution having a concentration of 1 mg/mL.

| Stirring rate (rpm) | Mean Z-average (nm) | Polydispersity index |
|---|---|---|
| 8000 | 214.3 | 0.252 |
| 16800 | 184.3 | 0.237 |
| 21200 | 170.2 | 0.224 |
| 25600 | 176.9 | 0.240 |

The particle size decreases with the increase of the stirring rate, so does the polydispersity index.

Particles in the size interval of interest (<220 nm) were obtained with the entire range of tested stirring rate.

Example 5

A volume of 8 mL of solution of PPS at the concentration of 1 mg/mL was added drop-wise to 10 mL of solutions of ChitoClear® TM1560 (degree of deacetylation 80%, molecular weight 66 kDa, Primex, Iceland) having different concentrations (0.5-5 mg/mL range), under constant stirring of 16800 rpm using a T10 basic Ultra-Turrax disperser (IKA, Germany). The mixing step was carried out at 40° C. for 2 minutes.

The particle size (mean zeta average), and size distribution (polydispersity index, PDI) of the formed particles were measured by dynamic light scattering technique (Zetasizer, Malvern Instrument, UK).

The obtained data are reported in Table 4.

TABLE 4

Particle size and size distribution of particles obtained 16800 rpm using a T10 basic Ultra-Turrax disperser as a function of concentration of the chitosan solution.

| Chitosan concentration (mg/mL) | Mean z-average (nm) | Polydispersity index |
|---|---|---|
| 0.5 | 151.1 | 0.161 |
| 1 | 212.4 | 0.181 |
| 1.5 | 239.9 | 0.238 |

TABLE 4-continued

Particle size and size distribution of particles obtained 16800 rpm using a T10 basic Ultra-Turrax disperser as a function of concentration of the chitosan solution.

| Chitosan concentration (mg/mL) | Mean z-average (nm) | Polydispersity index |
|---|---|---|
| 2 | 638.6 | 0.687 |
| 5 | Solid precipitate | — |

The particle size as well as the size distribution increases with the concentration of the chitosan solution. It can be observed that particles in the size interval of interest (<220 nm) can be obtained with chitosan concentration ≤1 mg/mL.

Example 6

A volume of 8 mL of solution of PPS at the concentration of 1 mg/mL was added drop-wise to 10 mL of solutions of ChitoClear® TM1854 (degree of deacetylation 60%, molecular weight 529 kDa, Primex, Iceland) having different concentrations (0.5-2 mg/mL range), under constant stirring of 16800 rpm using a T10 basic Ultra-Turrax disperser (IKA, Germany). The mixing step was carried out at 40° C. for 2 minutes.

The particle size (mean zeta average), and size distribution (polydispersity index, PDI) of the formed particles were measured by dynamic light scattering technique (Zetasizer, Malvern Instrument, UK).

The obtained data are reported in Table 5.

TABLE 5

Particle size and size distribution of particles obtained 16800 rpm using a T10 basic Ultra-Turrax disperser as a function of concentration of the chitosan solution.

| Chitosan concentration (mg/mL) | Mean z-average (nm) | Polydispersity index |
|---|---|---|
| 0.5 | 329.6 | 0.345 |
| 1 | 238.8 | 0.293 |
| 2 | 348.1 | 0.345 |
| 5 | Solid precipitate | — |

No particles in the size interval of interest (<220 nm) can be obtained with this chitosan at high molecular weight and low degree of deacetylation.

Example 7

A volume of 71.5 mL of solution of PPS at the concentration of 6.5 mg/mL was added drop-wise to 28.5 mL of solution of chitosan 95/50 (degree of deacetylation 97%, molecular weight 150 kDa, HMC, Germany) having a concentration of 6.5 mg/mL, under variable rotor rotation, ranging from 8000 to 30000 rpm using a T25 basic Ultra-Turrax disperser (IKA, Germany). The mixing step was carried out at 40° C. for 10 minutes and then the nanosuspension was kept in stirring for a further 10 minutes.

The particle size (mean zeta average), and size distribution (polydispersity index, PDI) of the formed particles were measured by dynamic light scattering technique (Zetasizer, Malvern Instrument, UK).

All particles presented a diameter out of the range of interest because namely, higher than 220 nm.

Example 8

A volume of 62.5 mL of solution of PPS at the concentration of 6.5 mg/mL was added drop-wise to 37.5 mL of solution of chitosan 95/50 (degree of deacetylation 97%, molecular weight 150 kDa, HMC, Germany), under variable rotor rotation, ranging from 8000 to 30000 rpm using a T25 basic Ultra-Turrax disperser (IKA, Germany). The mixing step was carried out at 40° C. for 10 minutes and then the nanosuspension was kept in stirring for a further 10 minutes.

The particle size (mean zeta average), and size distribution (polydispersity index, PDI) of the formed particles were measured by dynamic light scattering technique (Zetasizer, Malvern Instrument, UK).

No particles in the size interval of interest (<220 nm) were obtained since all particles presented a diameter higher than 1 µm.

Example 9

For comparative purpose, PPS—Chitosan gels were prepared by ionotropic gelation according to what is taught by Raspagni et al. (J. Controlled Release 148, 2010, e112-e124) by adding the PPS solution into a chitosan 95/50 solution (degree of deacetylation 97%, molecular weight 150 kDa, HMC, Germany). The concentration of the chitosan solution (50 mg/mL) and PPS solution (10 mg/mL) were kept constant; three e different weight ratios between the PPS and chitosan were adopted namely 0.5:1, 1:1 and 2:1.

The PPS solutions (2.5, 5, or 10 mL) were added drop-wise to 10 mL of chitosan solution at a constant rate of 0.5 mL/min under continuous stirring of 9500 rpm (T8 basic Ultra-Turrax disperser, IKA, Germany).

A viscous gel was obtained in all the three cases without formation of nano- or microparticles.

Example 10

A volume of 28.5 mL of solution of chitosan 95/50 (degree of deacetylation 97%, molecular weight 150 kDa, HMC, Germany) at the concentration of 4.5 mg/mL was added drop-wise to 71.5 mL of solution of PPS having a concentration of 8.5 mg/mL (ratio between the PPS and the chitosan 4.74:1 w/w or 5:2 v/v), under variable rotor rotation, ranging from 8000 to 30000 rpm using a T25 basic Ultra-Turrax disperser (IKA, Germany). The mixing step was carried out at 40° C. for 10 minutes and then the nanosuspension was kept in stirring for a further 10 minutes.

The obtained nanosuspension was then homogenized (High-Pressure Homogenizer, GEA Niro Soavi, Italy) at 35 cycles at 1200 bar.

The particle size (mean zeta average), and size distribution (polydispersity index, PDI) of the formed particles were measured by dynamic light scattering technique (Zetasizer, Malvern Instrument, UK).

The obtained particles presented a size of 201±3.1 nm and the PDI of 0.186±0.01.

Example 11

A volume of 23 mL of solution of chitosan 95/50 (degree of deacetylation 97%, molecular weight 150 kDa, HMC, Germany) at the concentration of 4.5 mg/mL was added drop-wise to 77 mL of solution of PPS having a concentration of 10 mg/mL (ratio between the PPS and the chitosan 7.44:1 w/w or 5:1.5 v/v), under variable rotor rotation, ranging from 8000 to 30000 rpm using a T25 basic Ultra- Turrax disperser (IKA, Germany). The mixing step was carried out at 40° C. for 10 minutes and then the nanosuspension was kept in stirring for a further 10 minutes.

The obtained nanosuspension was homogenized (High-Pressure Homogenizer, GEA Niro Soavi, Italy) at 35 cycles at 1200 bar.

The particle size (mean zeta average), and size distribution (polydispersity index, PDI) of the formed particles were measured by dynamic light scattering technique (Zetasizer, Malvern Instrument, UK).

Obtained nanoparticles resulted to be of 204.1±4.3 nm and the PDI of 0.191±0.01.

Example 12A nanosuspension was prepared as in Example 1 with a PPS concentration of 1 mg/mL.

The degree of complexation of PPS with chitosan in the nanoparticles was determined by quantifying the amount of free (uncomplexed) PPS in solution. The nanosuspension was filtered through filter with 0.1 μm pore diameter. The amount of free PPS was measured in the filtered supernatant by Electron Spray Ionization—mass spectrometry (4000 Qtrap, ABSciex, USA).

The complexed PPS was calculated as:

$$PPS\ complexed = \frac{total\ amount\ of\ PPS - free\ amount\ of\ PPS}{total\ amount\ of\ PPS} \times 100$$

The amount of complexed PPS resulted to be 99.6±0.14% of the nominal PPS dose in the nanoparticles.

Example 13

A nanosuspension was prepared as in Example 9 with a PPS concentration of 8.5 mg/mL.

The degree of complexation of PPS with chitosan in the nanoparticles was determined by quantifying the amount of free (uncomplexed) PPS in solution. The nanosuspension was filtered through filter with 0.1 μm pore diameter. The amount of free PPS was measured in the filtered supernatant by Electron Spray Ionization—mass spectrometry (4000 Qtrap, ABSciex, USA).

The complexed PPS was calculated as:

$$PPS\ complexed = \frac{total\ amount\ of\ PPS - free\ amount\ of\ PPS}{total\ amount\ of\ PPS} \times 100$$

The amount of complexed PPS resulted to be ≤80% of the nominal dose of PPS in the nanosuspension.

Example 14

Plasma concentration versus time curve were evaluated in an in-vivo pharmacokinetics study carried out in rats after oral administration of 1 mL of a PPS aqueous solution having a concentration 4.64 mg/mL (Form I) or 1 mL of the PPS/chitosan nanosuspension (PPS conc. 4.64 mg/mL). In the nanosuspension the ratio between the volume of solution of PPS (6.5 mg/mL) and of solution of chitosan (6.5 mg/mL) used for the production of the nanoparticles was 5:2 (v/v).

The obtained plasma concentration vs time curves are reported in FIG. 1.

The area under the curve for the nanoparticle formulation was 2593 min μg mL$^{-1}$ and for the PPS solution was 1306 min μg mL$^{-1}$. A higher $t_{max}$ (120 vs. 60 min) was also observed for the rats treated with the nanoparticles compared with rats treated with the PPS solution. This value afforded a relative bioavailability of about 200%.

Example 15

The nanosuspension prepared as in example 11 is added with mannitol (Perlitol® 200SD, Roquette, France) in ratio 3:1 on the PPS weight. After mannitol complete dissolution the suspension is spray dried with a Büchi B290 apparatus equipped with a spray nozzle of 1 mm diameter. The applied drying condition are:

inlet temperature 140° C.;
air flow 600 L/hour;
suspension feed rate 2 mL/min;
aspirator 35 m$^3$/hour.

The obtained powder is left in the collector for 15 minutes before further use.

Example 16

The nanosuspension prepared as in example 10 is added with mannitol (Perlitol® 200SD, Roquette, France) in ratio 3:1 on the PPS weight. After mannitol complete dissolution the suspension is poured in a glass cylindrical container and immediately placed in the chamber of a freeze drier (Alpha 2-4, Martin Christ, Germany), then the temperature is dropped to −40° C. and kept at this value for 1 hour to assure complete freezing of the suspension. Thereafter, the pressure in the chamber is lowered to 0.1 mbar. Then, the plate temperature is raised at −5° C. in 2 hours and kept at tis value for 12 hours (primary drying). Thereafter, the secondary drying is performed by lowering the pressure at 0.01 mbar and raising the temperature to 5° C. in 3 hours. These conditions are kept constant for 6 hours. Then the pressure of the chamber is raised to the ambient value (1000 mbar) by opening the vent valve. The sample is recovered and stored until further use.

Example 17

| Hard gelatin Capsules Size 0 - Quantitative composition | |
|---|---|
| Powder as in example 15 | 413.44 mg |
| Microcrystalline cellulose | 90 mg |
| Magnesium stearate | 2.5 mg |

The invention claimed is:

1. An Oral Composition comprising nanoparticles of a complex of Pentosan Polysulfate sodium with chitosan, wherein the nanoparticles have a diameter between 80 and 220 nm and wherein the chitosan has a degree of deacetylation between 78 and 99% and molecular weight between 30 and 400 kDa.

2. The composition according to claim 1 containing less than 20% by weight of non-complexed Pentosan Polysulfate sodium.

3. The composition according to claim 1 in form of a tablet, hard capsule, powder, solution, powder or syrup.

* * * * *